United States Patent [19]

Taylor et al.

[11] Patent Number: 5,364,691

[45] Date of Patent: Nov. 15, 1994

[54] ALK-1-ENYLOXY CARBONATES

[75] Inventors: Paul D. Taylor, West Milford; Kolazi S. Narayanan, Palisades Park, both of N.J.; Jeffrey S. Plotkin, Monsey, N.Y.

[73] Assignee: ISP Investments Inc., Wilmington, Del.

[21] Appl. No.: 490,854

[22] Filed: Mar. 9, 1990

[51] Int. Cl.$^5$ .................... C08F 2/50; C08F 18/24; C08F 26/02

[52] U.S. Cl. .................... 428/220; 427/506; 427/517; 522/15; 522/31; 522/96; 522/107; 522/170; 522/181; 522/108; 522/97; 526/301; 526/314

[58] Field of Search .................. 427/541, 506, 517; 526/314, 301; 525/404; 428/220; 522/31, 96, 97, 107, 108, 170, 181

[56] References Cited

U.S. PATENT DOCUMENTS

| | | | |
|---|---|---|---|
| 2,387,934 | 10/1945 | Muskat | 526/314 |
| 2,407,446 | 9/1946 | Pollack | 526/314 |
| 2,568,658 | 9/1951 | Pope | 526/314 |
| 2,821,539 | 1/1958 | Newman | 526/314 |
| 4,156,035 | 2/1979 | Tsao . | |
| 4,654,379 | 2/1987 | Lapin . | |
| 4,742,133 | 5/1988 | Tang | 526/314 |
| 4,783,544 | 11/1988 | Yokoshima | 526/314 |

OTHER PUBLICATIONS

J. A. Dougherty and F. J. Vara, L. R. Anderson, "Radcure '86": Conference Proceedings, Association for Finishing Processes, Baltimore, 1986, 15-1.

J. A. Dougherty and F. J. Vara, "Radcure Europe '87": Conference Proceedings, Association for Finishing Processes, Munich, West Germany, 1987, 5-1.

J. V. Crivelli, J. L. Lee, D. A. Conlon, "Radiation Curing VI: Conference Proceedings", Association for Finishing Processes, Chicago, 1982, 4-28.

S. C. Lapin, "Radcure '86: Conference Proceedings", Association for Finishing Processes, Baltimore, 1986, 15-15.

S. C. Lapin, "RadTech '88–North America: Conference (List continued on next page.)

Primary Examiner—Marion E. McCamish
Assistant Examiner—Arthur H. Koeckert
Attorney, Agent, or Firm—Marilyn J. Maue; Joshua J. Ward

[57] ABSTRACT

This invention relates to radiation curable alk-1-enyloxy carbonate reaction products of a hydroxylated compound having the formula A-ROH and a dialk-1-enyloxy carbonate having the formula

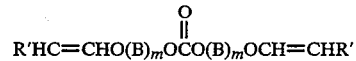

wherein R is a polymeric radical selected from the group of polyester, polyacetal, polyurethane, polyether, and polycarbonate, said polymers containing from about 10 to 50 repeating monomer units;

A' is a terminating moiety and is hydrogen, lower alkyl or hydroxy;

R' is hydrogen or lower alkyl;

B is a linear, branched or cyclic divalent radical having from 2 to 12 carbon atoms and is selected from the group of alkylene, mono or poly alkoxylated alkylene, alkenylene, alkynylene, arylene, alkarylene and aralkylene radicals, which radicals are optionally substituted with halo, lower alkyl, cyano, nitro or alkoxy and m has a value of from 1 to 10. The products of this invention are defined by the formula:

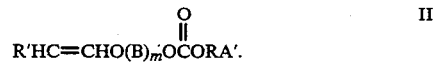

wherein A' is a terminating moiety and is hydrogen, lower alkyl or

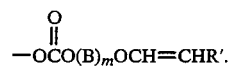

12 Claims, No Drawings

OTHER PUBLICATIONS

Proceedings" RadTech International, New Orleans, 1988, p. 395.

A. D. Ketley and Jung-Hsien Tsao, *J. Radiation Curing*, Apr. 1979, p. 22.

W. C. Perkins, *J. Radiation Curing*, Jan., 1981, p. 16.

P. C. Nelson and E. J. Moran, "RadTech '88–North America: Conference Proceedings", RadTech International, New Orleans, 1988, p. 120.

B. L. Brann, "RadTech Europe '89: Conference Proceedings", Radtech Europe, Florence, 1989, p. 565.

F. J. Vara and Jim Dougherty, Radcure '89 Conference Proceedings, "Concurrent Cationic/Free Radical Polymerization of Vinyl Ethers with Acrylate Functional Oligomers".

F. J. Vara and J. A. Dougherty, Water-Borne and Higher-Solids Coating Symposium, Feb., 1990, "Vinyl Ether in UV and EB Induced Cationic Curing".

ALK-1-ENYLOXY CARBONATES

In one aspect the invention relates to alk-1-enyloxy carbonates which are rapidly curable by cationically initiated radiation. In another aspect the invention relates to the use of said products as protective coatings or as photoresist materials.

BACKGROUND OF THE INVENTION

Free radical induced radiation curable coatings and films are normally formulated with acrylate monomer diluents and acrylate functional oligomers. The formulations usually contain minor amounts of additive ingredients such as surfactants, slip agents, defoamers, thickeners, and/or thixothopes. Representative oligomers are the acrylate functional end capped urethane polyesters, polyols and acrylate functional end capped bisphenol A epoxy and novalic epoxy resins.

Since acrylates are not conducive to cationically induced radiation curing, they require free radical systems which are oxygen inhibited unless reacted in an inert atmosphere, generally under a blanket of nitrogen. Although formulation with a photoinitiator which undergoes bimolecular reaction with a hydrogen donor minimizes the inhibitory effect of air, this benefit is realized at the expense of a greatly reduced cure rate. Also, it is found that polymerization or curing in free radical systems ceases almost immediately upon removal from the source of radiation; thus, the cured product often contains some unpolymerized components. Accordingly, it is an aim of research to develop an oligomer having the beneficial properties of acrylates but which is amenable to radiation curing at a rapid rate by cationically induced polymerization which is not oxygen inhibited and which permits continued polymerization after removal from the source of radiation exposure.

It has also been found that acrylate formulations when stored under normal condition require the addition of a free radical scavenger such as substituted hydroquinones and phenothiazine to achieve long term stability. However, after the stored coating is applied on a substrate, the inhibitory effect of the stabilizer significantly reduces the cure rate.

Finally, it is noted that the unsubstituted acrylates are sensitizers and skin irritants as well as being carcinogenic, so that specialized safety precautions must be taken to protect operators from exposure. Although alkoxylation has lessened irritancy of the acrylates, their carcinogenic properties are not reduced.

Accordingly it is an object of the present invention to overcome the above described deficiencies by employing an economical and commercially acceptable compound or composition and curing process.

Another object of this invention is to utilize a multifunctional cross-linking agent, which is itself a polymerizable viscous liquid and which assists rapid radiation curing when formulated with allyl, epoxide or acrylate monomers and oligomers.

Another object is to provide a non-toxic cross linkable compound which is suitably cured as a film or as a coating on a substrate and which possesses good adhesion, high abrasion resistance and resistance to chemical attack in both acid or basic media.

Still another object is to provide a more economical process for cross-linking monomeric or polymeric acrylates or epoxides within a few seconds which can be effected in the presence of air.

Another object is to provide a compound which is curable at a rapid rate by cationically induced radiation.

Yet another object is to provide a substrate coated with a rigid scratch resistant and chemical resistant coating.

These and other objects will become apparent from the following description and disclosure.

THE INVENTION

In accordance with this invention there is provided a polymerizable compound having the formula

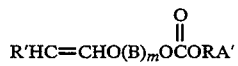     I.

which is the reaction product of a hydroxylated reactant (I) having the formula A-ROH and a dialkenyloxy carbonate coreactant (II) having the formula:

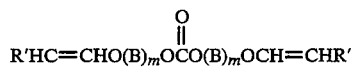     II.

wherein R is a polymeric radical selected from the group of polyester, polyacetal, polyurethane, polyether, and polycarbonate, said polymers containing from about 10 to 50 repeating monomer units;

A' is a terminating moiety and is hydrogen, lower alkyl or

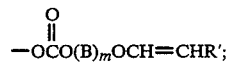

R' is hydrogen or lower alkyl;

B is a linear, branched or cyclic divalent radical having from 2 to 12 carbon atoms and is selected from the group of alkylene, mono or poly alkoxylated alkylene, alkenylene, alkynylene, arylene, alkarylene and aralkylene radicals, which radicals are optionally substituted with halo, lower alkyl, cyano, nitro or alkoxy and (m) has a value of from 1 to 10.

Reactant (I), AROH, includes hydroxylated compounds having the formulae:

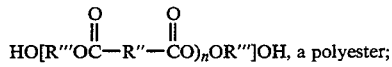

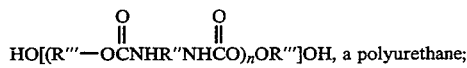

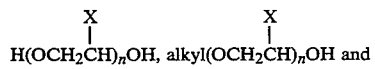

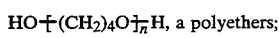

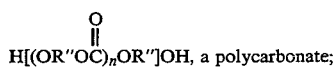

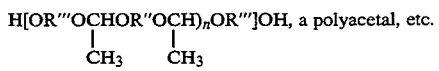

In the above formulae, X is hydrogen or methyl; R'' is $C_2$ to $C_{20}$ alkylene or arylene; R''' is $C_2$ to $C_{20}$ alkylene and n has a value of from about 10 to 50. Of these hydroxylated polymers, the polyethers, polyesters, polycarbonates and polyurethanes are preferred.

A general equation illustrating the synthesis of the present carbonate products of this invention is expressed as follows:

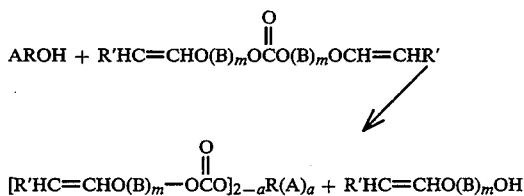

The dialkenyloxy alkyl carbonate coreactants (II) are those compounds described in copending application FDN-1757 U.S. patent application Ser. No. 491,395, filed Mar. 9, 1990, entitled ALKENYL ETHER CARBONATES, and are preferably those wherein R' is hydrogen or methyl, m is 1 and B is butylene, dimethylene cyclohexane or ethoxylated or propoxylated derivatives thereof.

Examples of suitable coreactants include bis(ethenyloxy butyl) carbonate, bis(ethenyloxy dimethylcyclohexyl) carbonate, bis(prop-1-enyloxy butyl) carbonate, bis(1-propenyloxy phenyl) carbonate, bis(ethenyloxy benzyl) carbonate, bis(ethenyloxy xylyl) carbonate and the polyethoxylated or polypropoxylated derivatives thereof, such as for example the polyethoxylated derivative of bis(ethenyloxy butyl) carbonate, having the formula

wherein p has a value of from 1 to 10.

The products of the present reaction comprise individual compounds or mixtures of compounds within the scope of the above formula I. Such mixtures or individual compounds are suitable for crosslinking with other monomers or oligomers by cationically induced radiation at a high cure rate. The individual compounds or mixtures of the present products are also homopolymerizable to a highly branched dense structure which provides superior scratch resistance and resistant to attack by acids, bases and solvents.

The reaction for synthesizing the above compounds is conducted in the presence of between about 0.01 and about 5 wt. %, preferably between about 0.1 and about 1 wt. % of a basic catalyst such as particulate sodium, potassium or lithium metal, sodium, potassium or lithium hydroxide, hydride or alkoxide, e.g. methoxide, and the like. The reactants may be diluted with up to 80% of a suitable inert solvent such as xylene, toluene, tetrahydrofuran, N-methylpyrrolidone, dimethylformamide, etc. Although dilution is usually recommended for more viscous reaction mixtures, it is also within the scope of this invention to carry out the reaction in the absence of solvent.

The reaction conditions include a temperature of from about 50° to about 200° C., a pressure of from about 1 mm Hg to about 100 atmospheres for a period of from about 0.5 to about 24 hours. Within the above operating parameters, between about 90° and about 120° C. under from about 1 to about 10 mm Hg for a period of from about 3 to about 7 hours are preferred. High conversions in excess of 80% are achieved by the present reaction.

The ratio of the A-ROH reactant to the dialkenyloxy alkyl carbonate reactant is as close to stoichiometry of the product desired as is convenient to maintain. Desirably, the amount of dialkenyloxy alkyl carbonate varies from about 1 to about 2 moles of carbonate per equivalent of hydroxyl groups in A-ROH. However, it is to be understood that excess amounts of the alkenyloxy alkyl carbonate, up to about a 10 mole excess, can be employed without detriment to the reaction; the only objection being that such high excesses of the carbonate reactant are wasteful and inefficient. Products of the synthesis product mixture can be separated by any conventional means, e.g. fractional distillation, if desired.

The above compounds or mixtures, either alone or formulated in admixture with other copolymerizable monomers or oligomers in amounts up to about 50%, can be applied a substrate in a thickness of from about 0.1 to about 20 mils, preferably from about 0.5 to about 10 mils. Suitable substrates include glass, ceramic, metal, plastic, wood, masonary and fabrics. The coated material is then subjected to curing from a source of radiation.

The other copolymerizable monomers with which the present products can be mixed include a vinyl ether, epoxide, acrylate or vinyloxy alkyl urethane monomer or polymer to incorporate and combine the advantages of instant compounds with the beneficial properties of those coating materials which otherwise would not be amenable to cationic radiation curing. Specific examples of monomers or polymers with which the present products can be combined to form coatings include 1,4-butanediol diglycidyl ether; 3,4-epoxycyclohexyl methyl-3,4-epoxy cyclohexane carbonate; the diglycidyl ethers of bisphenol A or bisphenol F; the polyglycidyl ethers of phenol-formaldehyde, e.g. epoxy novolac resins, vinyl cyclohexane epoxide, alkyl methacrylates and acrylates, vinyloxy butyl urethane and compounds disclosed in the HANDBOOK OF EPOXY RESINS by Henry Lee and K. Neville, published by McGraw Hill, 1967 and other functional monomers and polymers which possess properties beneficial in durable protective coatings. When such comonomeric coatings are employed, the mixture contains at least 25% of the present carbonate or mixtures of carbonates. These mixtures can also contain a surfactant such as a silicone or fluorocarbon surfactant, e.g. a fluoroaliphatic polymeric ester (FC-430 supplied by Minnesota, Mining and Manufacturing Co.).

The homopolymerized and copolymerized products of this invention have an extremely high cross-linked density and thus display superior resistance to solvents, acids and bases and form hard abrasion resistant films and coatings, possessing good substrate substantivity. The individual products of this invention, as monomers or oligomers or as mixtures thereof are also useful as chemical intermediates and as materials which, upon hydrolysis, are capable of forming hydrogels. Also, because of their high radiation sensitivity, the present compounds are suitable as photoresist materials.

Curing is effected in the presence of a cationic photoinitiator such as an onium salt, for example the triphenyl sulfonium salt of phosphorous hexafluoride, diphenyl iodonium salt, tetrazolium chloride, phenyl onium salts or aryl alkyl onium salts and the like or any of the photoinitiators described by James A. Crivello et al., (RA- DIATION CURING VI CONFERENCE PROCEEDINGS, 1982, pages 4-28 to 4-39, Chicago) in the article entitled "New Monomers for Cationic UV-Curing". The amount of initiator employed is generally between about 0.05 and about 5 wt. %, preferably between about 0.1 and about 2 wt. % with respect to reactants. However, initiator mixtures of the above named cationic initiators and a free radical initiator can also be employed to provide a hybrid initiated system. Suitable free radical initiators include 1-hydrocyclohexyl phenyl ketone (e.g. IRGACURE 184), 2-hydroxy-2-methyl-1-phenyl-1-propan-1-one (DAROCUR 1173), 2,2-dichloro-1-(4-phenoxyphenyl) ethanone (SANDORAY 1000) and the like. Other free radical and cationic initiators which are suitably employed in this invention are those described by M. J. M. Abadie, Advantages and Development of Photochmemical Initiators, in the European Coatings Journal 5/1988 pages 350–358. When initiator mixtures are employed, the free radical component can comprise up to 75%, preferably between about 30 and about 70%, of the photoinitiator component. A particularly preferred initiator mixture includes between about 30 wt. % and about 40 wt. % of FX-512 and between about 60 and about 70% of IRGACURE 184. The present cationic initiator or cationic/free radical mixtures are recommended for cross linking blends which include the present vinyl ether carbonate and an acrylate resin together with a viscosity lowering amount of a polymerizable vinyl ether or epoxide diluent. When the blend includes an acrylate, initiator mixtures are recommended. The curing is accomplished within a few seconds, most often within a period of less than one second, by exposure to a source of radiation such as UV light exposure at 100 to 1500, preferably at 200 to 600, millijoules/cm$^2$. Equivalent dosages for curing are employed when using alternative radiation sources, such as lazer emission or electron beam exposures. For example, curing with an electron beam is carried out at between about 0.5 and about 20, preferably between about 1 and about 10 megarads. Specific techniques for radiation curing are well known, thus further amplification is not required.

Having thus described the invention reference is now had to the accompanying examples which illustrate preferred embodiments but which are not to be construed and limiting to the scope of the invention as more broadly defined above and in the appended claims.

EXAMPLE 1

In a 250 ml, one necked, round bottom flask, 80 g. (0.08 mole) polyethylene glycol with an average molecular weight of 1000 was charged along with 56 g. bis(ethenyloxybutyl) carbonate (0.22 mole) and 0.2 g. sodium ethoxide. The flask was heated under vacuum at 3 mm Hg, at 100°–105° C. in a Kugelrohr apparatus for a period of 7 hours after which a total of 22.5 g. distillate was collected. The distillate was identified by GC analysis as a mixture containing 75–80% hydroxybutyl vinyl ether and 20–25% of bis(ethenyloxybutyl) carbonate. About 90% conversion was achieved.

The contents of the flask containing the major product of the reaction was treated with 2 g. (Nuchar) charcoal and filtered at about 45° C. The filtrate solidified on standing yielding 98 g. of a clear colorless waxy solid which was identified as product having the formula

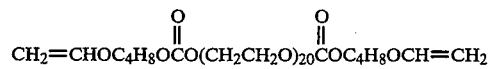

by $^1$H NMR and IR spectral analysis, a conversion of 87.6% was achieved.

EXAMPLE 2

In a 100 ml, one-necked, round bottom flask, 20 g. of Duracarb 120 (a hydroxy terminated lower alkyl polycarbonate of molecular weight ~850 g/mol) and 125 g. bis(ethenyloxybutyl) carbonate were mixed together with 0.1 g. of sodium methoxide. The contents of the flask was heated to 100° C. while under a vacuum of 3 mm Hg. After 3 hours, 3.4 g. of hydroxybutyl vinyl ether by-product had been distilled from the reaction mixture.

The contents of the flask containing the product of this invention was treated with 1 g. of (Nuchar) charcoal and filtered at 45° C. Upon standing the filtrate solidified to give 25 g. of a white, waxy solid. Analysis by $^1$H NMR indicated the polycarbonate bis(ethenyoxybutyl) end capped product.

What is claimed is:

1. A radiation curable composition containing a cationic photoinitiator, between about 0 and about 75 wt. % of a polymerizable monomer or oligomer which is not normally curable by cationically induced radiation curing and a polymer having the formula

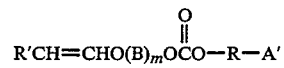

wherein R is a polymeric radical selected from the group of polyester, polyacetal, polyurethane, polyether, and polycarbonate, said polymers containing from about 10 to 50 repeating monomer units;

A' is a terminating moiety and is hydrogen, lower alkyl or

R' is hydrogen or lower alkyl;

B is a linear, branched or cyclic divalent radical having from 2 to 12 carbon atoms and is selected from the group of alkylene, mono or poly alkoxylated alkylene, alkenylene, alkynylene, arylene, alkarylene and aralkylene radicals, which radicals are optionally substituted with halo, lower alkyl, cyano, nitro or alkoxy; and (m) has a value of from 1 to 10.

2. The composition of claim 1 wherein said photoinitiator is predominantly triphenyl sulfonium hexafluorophosphate.

3. The composition of claim 1 wherein R' in the formula of said polymer is hydrogen and (m) is one.

4. The composition of claim 3 wherein B in the formula of said polymer is butylene.

5. The composition of claim 3 wherein B in the formula of said polymer is —CH$_2$—C$_6$H$_{10}$—CH$_2$—.

6. The composition of claim 1 wherein said polymer is a mixture of polymers having the described formula.

7. The process which comprises applying to a substrate an effective protective coating of the composition of claim 1 and curing said coating on said substrate by exposure to an effective curing amount of radiation.

8. The process of claim 7 wherein said coating is exposed to UV light at a dosage of between about 100 and about 1500 millijoules/cm$^2$ for a period of not more than one second.

9. The process of claim 7 wherein said coating is exposed to electron beam dosage of between about 0.5 and about 20 megarads for a period of not more than one second.

10. The product of the process of claim 8.

11. The product of the process of claim 9.

12. The product of the process of claim 17 wherein the coating on said substrate has a thickness of from about 0.1 to about 20 mils.

* * * * *